United States Patent [19]
Loeser

[11] Patent Number: 5,632,753
[45] Date of Patent: May 27, 1997

[54] SURGICAL PROCEDURES

[76] Inventor: Edward A. Loeser, 8646 Oak Valley Dr., Sandy, Utah 84093-2015

[21] Appl. No.: 416,217

[22] Filed: Apr. 4, 1995

Related U.S. Application Data

[63] Continuation-in-part of Ser. No. 998,950, Dec. 31, 1992, Pat. No. 5,403,346.

[51] Int. Cl.⁶ .................................................. A61B 17/08
[52] U.S. Cl. .................... 606/151; 606/157; 606/158; 606/213; 606/191; 128/898
[58] Field of Search ................................ 606/151, 157, 606/158, 191, 213, 215, 216, 218, 228, 232; 128/898

[56] References Cited

U.S. PATENT DOCUMENTS

| | | |
|---|---|---|
| 2,764,159 | 9/1956 | Masci et al. . |
| 3,123,077 | 3/1964 | Alcamo . |
| 3,225,766 | 12/1965 | Baptist et al. . |
| 3,463,158 | 8/1969 | Schmitt et al. . |
| 3,527,841 | 9/1970 | Wicker, Jr. et al. . |
| 3,564,078 | 2/1971 | Wicker, Jr. et al. . |
| 3,570,497 | 3/1971 | Lemole . |
| 3,577,601 | 5/1971 | Mariani et al. . |
| 3,636,956 | 1/1972 | Schneider . |
| 3,739,773 | 6/1973 | Schmitt et al. . |
| 3,759,264 | 9/1973 | Coover, Jr. et al. . |
| 3,772,420 | 11/1973 | Glick et al. . |
| 3,883,901 | 5/1975 | Coquard et al. . |
| 4,271,838 | 6/1981 | Lasner et al. . |
| 4,548,202 | 10/1985 | Duncan . |
| 4,693,246 | 9/1987 | Reimels . |
| 4,730,615 | 3/1988 | Sutherland et al. . |
| 4,773,421 | 9/1988 | Davis . |
| 4,836,205 | 6/1989 | Barrett . |
| 4,890,615 | 1/1990 | Caspari et al. . |
| 4,901,721 | 2/1990 | Hakki . |
| 4,901,722 | 2/1990 | Noguchi . |
| 4,932,962 | 6/1990 | Yoon et al. . |
| 4,935,027 | 6/1990 | Yoon . |
| 4,950,284 | 8/1990 | Green et al. . |
| 4,950,285 | 8/1990 | Wilk . |
| 4,957,498 | 9/1990 | Caspari et al. . |
| 4,961,741 | 10/1990 | Hayhurst . |
| 4,981,149 | 1/1991 | Yoon et al. . |
| 5,015,250 | 5/1991 | Foster . |
| 5,053,047 | 10/1991 | Yoon . |
| 5,074,874 | 12/1991 | Yoon et al. . |
| 5,084,058 | 1/1992 | Li . |
| 5,100,418 | 3/1992 | Yoon et al. . |
| 5,102,421 | 4/1992 | Anspach, Jr. . |
| 5,403,346 | 4/1995 | Loeser ................................ 606/228 |

OTHER PUBLICATIONS

*Novak's Textbook of Gynecology*, "Chapter 1: History, Examination and Operation", pp. 26–27.

*XIV. Family Planning*, "Chapter 62, Surgical Contraception", pp. 1353–1357.

*Primary Examiner*—Michael Buiz
*Assistant Examiner*—Mark S. Leonardo
*Attorney, Agent, or Firm*—Trask, Britt & Rossa

[57] ABSTRACT

A method of occluding a vessel including: cinching the vessel with a ligature comprising a flexible elongate base structure having a longitudinal axis, a needle end, and a second end, a collar for receiving a needle and affixed elongate base structure, positioned on the second end, and a node for interacting with the collar, the node positioned on the elongate base structure, between the needle and second ends, transverse to the longitudinal axis and having a proximal and a distal edge with respect to the needle end of the flexible elongate base structure, a portion of the node's proximal edge relative the needle end of the flexible elongate base structure being perpendicular to the elongate base structure's longitudinal axis. The method is ideally suited for performing a tubal (fallopian tube) ligation for reproductive control. In such a case, the fallopian tube is cinched sufficiently to block passage of an ovum through the fallopian tube's lumen, but is insufficiently occluded to unduly restrict blood circulation through the fallopian tube. In such a method, the ligature may be impregnated with contraceptive compound (e.g. a contraceptive steroid such as a progestogen) in order to prevent implantation of an ovum which already passed through the fallopian tube's lumen.

20 Claims, 3 Drawing Sheets

SURGICAL PROCEDURES

RELATED APPLICATIONS

This application is a continuation-in-part of U.S. Ser. No. 07/998,950 filed on Dec. 31, 1992, now U.S. Pat. No. 5,403,346 (Apr. 4, 1995), the contents of which are incorporated herein by this reference.

TECHNICAL FIELD

The invention relates to a suture device useful in surgery in general and to processes for using a self-affixing suture assembly in particular.

BACKGROUND

Laparoscopic tubal sterilization techniques such as unipolar electrocoagulation, bipolar electrocoagulation, tubal ring occlusion, and the use of a spring-loaded tubal clip are disclosed in *Novak's Textbook of Gynecology*.

As described in *Novak's*, the tubal ring occlusion was first described by Yoon et al. in 1974 and uses a silicone rubber band for the occlusion of a small knuckle of uterine tube just lateral to the cornu of the uterus.

The use of a spring-loaded tubal clip involves utilizing a very small inert clip modified with a metal spring to provide sustained apposition under pressure. This technique is reported to result in minimal destruction of the uterine tube.

All of these techniques have some drawbacks. For instance, as described in *Novak's*, these techniques are all associated with some risk of subsequent pregnancy due to, for example, carrying out the procedure in the luteal phase at a time when the fertilized ovum has passed through the uterine tube into the endometrial cavity. Furthermore, the spring-loaded tubal clip can dislodge, leaving a foreign metallic object in the woman's body besides subjecting her to a risk of an unintended pregnancy.

Another problem associated with these techniques is that they are expensive to have reversed, and the restoration process is not always successful.

It would be an improvement in the art to have a tubal sterilization technique which was more easily reversible and which would have a smaller chance of causing tissue damage and allowing for an unintended pregnancy.

DISCLOSURE OF THE INVENTION

The invention includes a method of occluding a vessel. The method includes cinching the vessel with a ligature comprising a flexible elongate base structure having a longitudinal axis, a needle end, and a second end, a collar for receiving a needle and affixed elongate base structure, positioned on the second end, and a node for interacting with the collar, the node positioned on the elongate base structure, between the needle and second ends, transverse to the longitudinal axis and having a proximal and a distal edge with respect to the needle end of the flexible elongate base structure, a portion of the node's proximal edge relative the needle end of the flexible elongate base structure being perpendicular to the elongate base structure's longitudinal axis.

The method is ideally suited for performing a tubal (fallopian tube) ligation for reproductive control. In such a case, the fallopian tube is cinched sufficiently to block passage of an ovum through the fallopian tube's tureen, but is insufficiently occluded to unduly restrict blood circulation through the fallopian tube. In such a method, the ligature may be impregnated with contraceptive (e.g. a contraceptive steroid such as a progestogen) or other (e.g. antibiotic, anesthetic) compound in order, for example, to prevent implantation of an ovum which already passed through the fallopian tube's lumen.

A process for occluding a fallopian tube includes providing a ligature comprising a flexible elongate base structure having a longitudinal axis, a needle end, and a second end, a collar for receiving a needle and affixed elongate base structure, positioned on the second end, and a node for interacting with the collar, the node positioned on the elongate base structure, between the needle and second ends, transverse to the longitudinal axis and having a proximal and a distal edge with respect to the needle end of the flexible elongate base structure; inserting the needle end through mesosalpinx associated with the fallopian tube; encircling the fallopian tube with the ligature; placing the needle end and affixed elongate base into the collar; and cinching the ligature about the fallopian tube to prevent passage of ova therethrough.

The process can further include cinching a second ligature, in a spaced relationship (e.g. 0.5 to three centimeters) along the fallopian tube from the first ligature, about the same fallopian tube. The process can still further include cutting through the fallopian tube if permanent sterilization is desired.

In one embodiment, the ligature of the process further includes an arced portion along the elongate base, such that when the ligature is cinched about the fallopian tube, a loop (having a diameter of 0.5 to two centimeters), non-contiguous with the fallopian tube, exists in the ligature.

The ligature may be formed of a biodegradable material, which is especially useful if the process is to be performed post-partum.

The method may also be practiced on other vessels such as the vas deferens, veins, cystic ducts of a gall bladder, and arteries.

The process can be conducted laparoscopically or endoscopically.

In one embodiment, the elongate base structure is at least partially formed of a biodegradable material (e.g. PLAGA).

A hinged flap may be positioned within the collar for allowing unidirectional movement of base structure and associated node therethrough.

The process is to be practiced on the vessels of mammals, including women.

BRIEF DESCRIPTION OF THE FIGURES

In the drawings, which depict presently preferred embodiments of the invention and in which like reference numerals refer to like parts in different views.

BEST MODE OF THE INVENTION

A preferred ligature for use with the invention includes an elongate base structure having a needle end, a collar end, and at least one node for interacting with the collar end. The node is positioned on the elongate base structure transverse to the base structure's longitudinal axis, and has a proximal and a distal edge with respect to the needle end (a "leading" and "trailing" edge, respectively). In the invention, a portion of the node's proximal edge is perpendicular to the elongate base structure's longitudinal axis, thus acting to prevent further cinching of the device once it has been finally placed. The distal edge of the node may also be wholly or partially perpendicular to the elongate base structure's longitudinal axis.

Between the proximal and distal edges of a single notch is a top surface. This top surface will usually be planar or convex. A planar top surface can be, but need not be, parallel to the base structure's longitudinal axis.

In one embodiment of the device, the elongate suture has multiple nodes. The nodes will then generally be positioned in a spaced relationship along the longitudinal axis of the suture cord, thus forming planar notches between the nodes. These notches can be sized to allow the collar or other structure to move along the longitudinal surface to a very limited extent to give the suture some "play", thus preventing possible tissue damage when the stitched tissue moves (e.g. by curing into the local tissue surrounding the stitches). In such a case, the planar notch will generally be parallel to the elongate suture's longitudinal axis.

A ligature may also have an elongate surface with evenly spaced lateral ribs traversing the surface and an aperture, collar or other means, associated with one end of the ligature, for impeding movement of the ligature in one direction through the aperture while still allowing movement in the direction opposite to the impeded direction. Between the lateral ribs are notches. The notches will, in cross-section, lay substantially parallel to the elongate surface's longitudinal axis. The aperture is sized to encase the notch while still allowing limited bi-directional longitudinal movement of the aperture in the area of the notch between the ribs.

Figure 1:
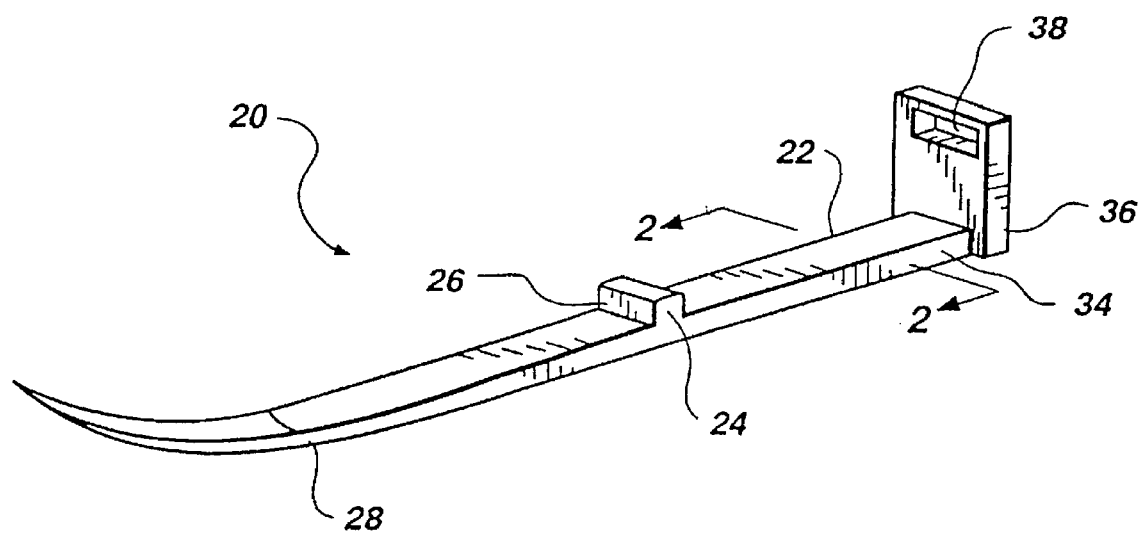
FIG. 1 is an enlarged isometric view of a ligature according for use with one embodiment of the invention.
Figure 2:
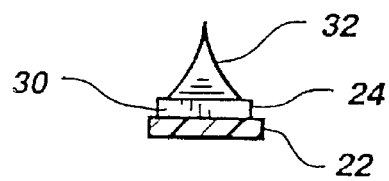
FIG. 2 is an enlarged cross-section of the ligature of FIG. 1 taken along section lines 2—2 from FIG. 1.

As shown in FIG. 1, a suture, generally 20, has a base structure 22. This base structure 22 may be of various cross-sections, e.g. circular, rectangular, square, or elliptical, although a rectangular one is depicted (FIG. 2). The suture, generally 20, will typically vary in length from two to sixty centimeters, preferably from three to 10 centimeters. The base structure will preferably have a width or diameter varying from 0.1 to three millimeters, but preferably one to two millimeters. In one preferred embodiment, the base structure has a uniform cross-sectional shape and dimension along its longitudinal axis.

The base structure is flexible enough to be stitched and is preferably made of a material strong enough to hold two pieces of tissue together after stitching. Acceptable materials for surgical sutures include those listed in the generalized monograph of the *United States Pharmacopeia*. These include absorbable and nonabsorbable sutures.

Examples of absorbable sutures include surgical gut ("catgut") and synthetic absorbable sutures such as thermoplastic polymers derived from condensing the cyclic derivative of glycolic acid (glycolide) and mixtures of glycolide and cyclicized lactic acid (lactide) (e.g. PLAGA). Materials and methods for making polyglycolic and polylactic are disclosed in U.S. Pat. Nos. 3,463,158; 3,739,773; 3,772,420; and 3,636,956, the contents of which are incorporated by this reference. Other absorbable polymers are disclosed in U.S. Pat. Nos. 3,225,766 and 3,883,901 (absorbable polyesters), U.S. Pat. No. 2,764,159 (absorbable cellulose glycolic acid ethers), and U.S. Pat. Nos. 3,527,841; 3,564,078; and 3,759,264 (esters of $\alpha$-cyanoacrylic acid), the contents of all of which are incorporated by this reference. Examples of nonabsorbable sutures include silk, dermal silk sutures (e.g. coated with tanned gelatin), nylon, polyester fiber, polyolefin fibers, silver, and stainless steel. PLAGA fibers can be melt extruded.

Figure 3:
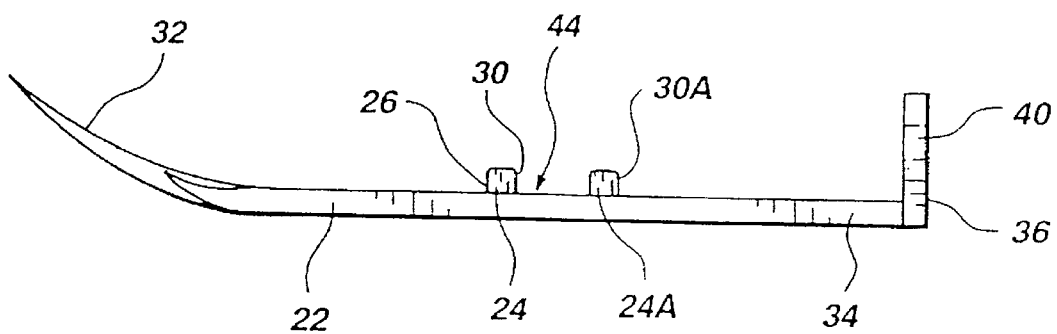
FIG. 3 is an enlarged side-view of a ligature for use with one embodiment of the invention.

Positioned on the surface of the base structure 22 is a node 24 (or rib). This node 24 has an edge 26 proximate the needle end 28 of the suture. This proximal edge 26 sits perpendicular to the longitudinal axis of the base structure at the point of its association with the base structure (FIG. 3). It also has a distal edge 30 (with respect to the needle end 28 and any associated needle 32 (FIG. 2)). A rib or node may be integrally formed together with the base structure, or may be a separate piece affixed or attached to the base structure.

The diameter or cross-sectional area of the base structure with nodes will preferably be as close as possible to that of a conventional ligature to prevent unnecessary tissue damage. In a preferred embodiment, the nodes add less than half a millimeter to the total diameter of the base structure.

On the end 34 of the base structure 22 distal to the needle 32 is a latch collar 36 or other structure for interacting with the node 24 or nodes 24, 24A (FIG. 3). The latch collar 36 or similar structure acts to prevent withdrawal of the needle 32 and base structure 22 once they have been inserted into the aperture 38. In order to prevent withdrawal of the base structure, a flange, hinged flexible flap or member, latch 40 or similar structure is preferably associated with the aperture 38. The height of the collar structure is typically chosen to adequately span the wound and accommodate the aperture. The use of a flap placed within the aperture or collar is especially preferred since it allows for relatively easy cinching of the device without the need for undue tension which might cause tissue damage during placement.

The latch collar 36 may be formed of the same material as the base structure. This is especially the case when the structure is intended to be absorbable. Alternatively, the latch collar, or portions of it (e.g. the flap), may be formed of different materials if so desired. When the latch collar is made of the same material as the base structure, it can be integrally formed with the base structure.

FIG. 3 depicts another embodiment of the device having two nodes 24, 24A. Between the two nodes is a planar notch 44 having a length along the longitudinal axis of the base structure 22 at least that of the thickness of the latch collar 36. The length of the notch can be selected to provide very limited play of the collar about the notch (e.g. from 0.1 to one millimeter). In the embodiment depicted in FIG. 3, the nodes 24, 24A have a convex top surface to facilitate their entry and placement in the aperture 38, although planar, concave, and other shapes will also work.

In the embodiment depicted in FIGS. 1–3, the nodes or ribs are generally block-shaped and run perpendicular to the longitudinal axis of the suture. In cross-section, they will generally be square. The general block shape of such a rib is particularly advantageous when biodegradable suture material is used to form the ribbed suture. This advantage arises since during degradation of the suture material in the body, it will take some time for the ribs to erode sufficiently to allow the suture to back out of the latch collar end, thus preventing possible premature separation of the stitched tissues. In contrast with pointed nodes, the tip of the node can erode first, thus freeing, possibly prematurely, the latch collar to slide up the base structure and opening the wound.

Figure 4:
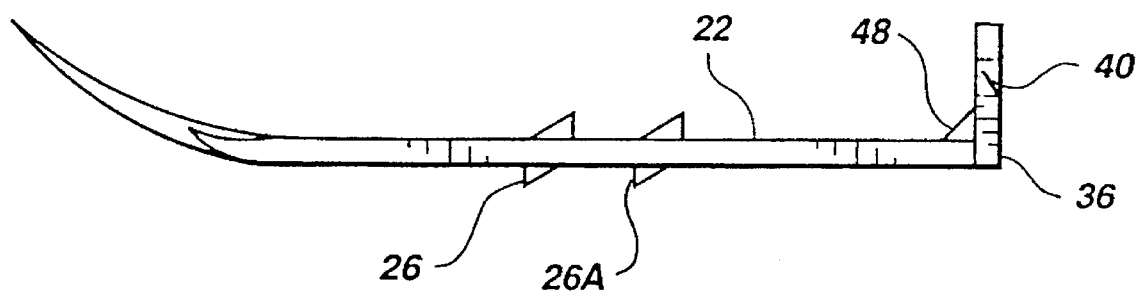
FIG. 4 is an enlarged side-view of a ligature for use with one embodiment of the invention.
Figure 5:
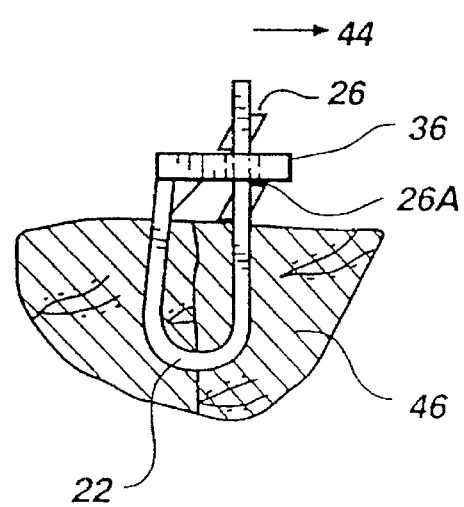
FIG. 5 is an enlarged elevational view of a stitch completed by the device of FIG. 4 with the needle removed.
Figure 6:
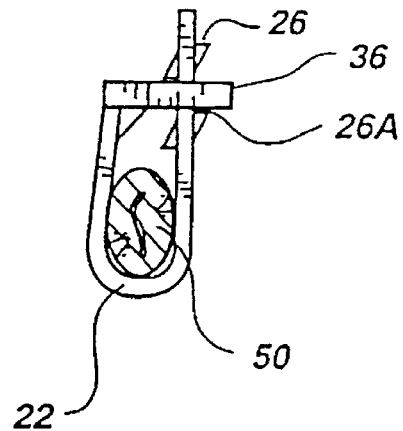
FIG. 6 is an enlarged view of a tubal ligation completed by a device according to the invention.

FIG. 4 depicts another embodiment of the device. In this embodiment, the proximal edges 26, 26A are mounted on the opposite side of the base structure 22 than that shown in the previously described embodiments (FIGS. 1 to 3). This device also has at the base of the collar a small thickening or other structure for abutment 48 against the tissue 46 once the suture has been placed (FIG. 5). This structure steadies the suture somewhat after placement.

In embodiments where the device has several nodes, the spacing between the distal edge of one node and the proximal edge of the next will typically vary from 0.1 to one millimeter, thus forming several notches between the spaced ribs. Preferably the nodes will be evenly spaced.

In one embodiment, the notch portions between the evenly spaced ribs are pre-chosen, allowing limited movement of the suture about the latch collar end. This movement gives the device some flexibility and decreases rigidity, which can result in undue pain or tissue damage when the stitched tissue moves.

To use any of the depicted devices, the surgeon first prepares and orients the suture assembly to the extent necessary. The surgeon then pierces the tissue to be sutured with the needle 32 and draws it through the tissue (e.g. with forceps or a needle holder) with the flexible base structure 22 following up and cinching the wound. The needle 32 is then inserted into the aperture 38 which is sized and shaped to accept the base structure and accompanying node(s). In a device having multiple nodes 24, 24A, the surgeon passes the collar end by an appropriate number of nodes to firmly cinch the tissue together. For a device such as that, this may require the surgeon to pull the base structure in a direction opposite to that of direction 44 (FIG. 5). The needle and appropriate amount of ligature is then cut off. The device, even though flexible, still tends to open, thus pushing the base structure in direction 44. Thus when tissue 46 moves, potentially driving the base structure further into the aperture 38, the proximal edge 26A butts up against the latch collar 36, preventing the device from further constricting the healing tissue 46.

Figure 7:
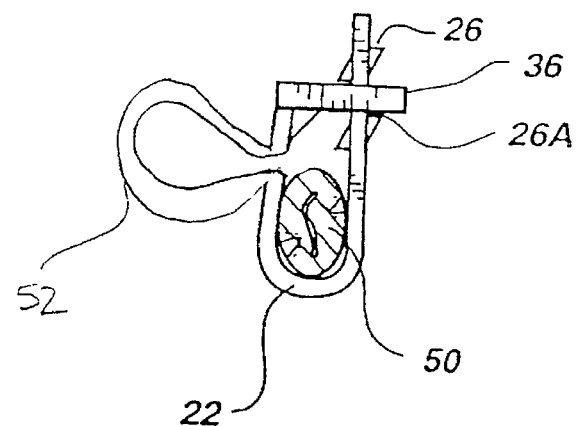
FIG. 7 is an enlarged view of a tubal ligation completed by a device according to the invention.

As depicted in FIG. 7, a preferred ligature according to the invention includes a base structure 22, a collar 36, and nodes 26, 26A. The ligature cinches a vessel 50, and includes a "loop" 52 formed in the base structure. This loop 52 is generally a rigid structure which is preferably made of a non-biodegradable material (e.g. polypropylene). More than one loop may be used (not shown). This ligature may be placed laparoscopically about a, for example, fallopian tube.

After placement (e.g. cinching about a fallopian tube to prevent passage of an ovum or sperm through the lumen of the tube 50), the tube may be restored by cutting the base structure through the loop 52. Again, such cutting may be done laparoscopically. The ligature is then removed from the body cavity. Such a ligature may be formed to include a radio-opaque substance (e.g. barium sulfate) so that the body cavity may be examined by X-ray to ensure that all pieces of the device have been removed.

After the ligature has been removed, a "tuboplasty" may be performed on the fallopian tube in an attempt to open the lumen of the fallopian tube. A balloon catheter is inserted up the fallopian tube, and the balloon inflated at the portion of the tube whereat the ligature was placed. If the tube was cut during placement of the ligature, a stint may be placed between the two portions (e.g. by microsurgical techniques).

The device can be used for various surgical procedures. When a bioabsorbable material is used, the procedure is temporary and may not require surgery to reopen the tubes. When the suture is not made of a bioabsorbable material, the device is especially useful for a Marshall-Marquette bladder suspension, bowel surgery, or for fastening a mesh during e.g. a hernia operation (see, e.g. U.S. Pat. No. 4,548,202 for a description of mesh having flexible filaments).

Various changes to the device can be made without departing from the spirit of the invention. For example in the case of a base structure having a circular cross-section, concentric ridges having a leading edge at least partially perpendicular to the longitudinal axis of the base structure, of preferably uniform height and dimension and evenly spaced from each other may extend around the surface of the base structure.

A kit according to the invention may contain an eyed needle together with several ligatures according to the invention. Alternatively, a kit according to the invention can contain several sutures to which respective needles have been attached together with a device for cutting off the needle and excess suture material (e.g. using a suture cutter such as that described in U.S. Pat. No. 4,271,838 to Lasner et at. (Jun. 9, 1981)) at a point within the subject's body.

A needle for use with the invention is preferably an eyeless needle. An eyeless needle may be manufactured with an open channel into which the ribbed suture is placed, and the channel swaged around the suture. Alternatively, a "seamless" needle may be used, which has a very delicate hole drilled in the shank, and the shank is pressed firmly about the suture. In one embodiment, the eyeless needle can be removed from the strand by gently tugging on it. Needles such as those disclosed in U.S. Pat. No. 4,981,149 to Yoon et at. (Jan. 1, 1991) and U.S. Pat. No. 4,901,722 to Noguchi (Feb. 20, 1990) may be used.

A preferred device for cutting off the needle and unused portion of the suture includes a barrel sized to accept the length of excess suture being used and associated with two separate sets of levers which, when actuated, provide the mechanical action necessary to collect the needle and snip off the base structure of the suture.

At the end of the barrel of such a cutting device (distal to the user), there is an orifice or opening sized to receive a needle of the size being used. This distal end of the cutting device is inserted into a cavity in the subject and, after the suture has been cinched, the needle is placed within the orifice. Actuating a first set of levers causes two rubber type geared wheels to rotate in opposite directions drawing the needle in and accepting it and the associated suture material into the barrel. A sufficient amount of suture material is, of course, left behind to provide sufficient tension for the stitched tissue to keep in apposition and heal.

Alternatively, the cutting device may employ a series of trapping flaps to enclose and contain the needle or needles and excess suture material. A second set of levers actuates two scissor blades just inside the orifice (and distal to the set of wheels) which cut the suture at the desired length, releasing the remaining portion of the suture. The procedure can be repeated, and the excess suture material and attached needles remain within the device until disposal occurs. When the device is full of needles and excess suture material or when the surgery is over, it is discarded.

The ligature may be impregnated with various biologically active substances such as contraceptive steroids (e.g. progestogens, estrogens or mixtures thereof), antibiotics, local anesthetics, heparin, anti-thrombin agents, and other substances.

EXAMPLES

Example I

Two devices, made as depicted in FIG. 7 (of a non-biodegradable material), are laparoscopically placed on each of the fallopian tubes of a healthy, fertile female.

Example II

Four devices, made as depicted in FIG. 3 (and of a biodegradable material), are cinched about both fallopian tubes (two per fallopian tube) of a healthy, human female one day post-partum. The needle ends of the devices are clipped from the base structure and removed from the body cavity. Contraception is provided for several months.

Example III

A device made according to FIG. 4 (made of a non-biodegradable material) is cinched about the vas deferens of a healthy male.

Although the invention has been described with regard to certain preferred embodiments, the scope of the invention is defined by the appended claims.

What is claimed is:

1. A process for occluding a vessel selected from the group of vessels consisting of fallopian tubes, vas deferens, veins, cystic ducts of a gall bladder and arteries, said process comprising:

cinching the vessel with a ligature comprising:
    a flexible elongate base structure having a longitudinal axis, a needle end, and
    a second end,
    a collar for receiving a needle and affixed elongate base structure, positioned on said second end, and
    a node for interacting with the collar, said node positioned on said elongate base structure, between said needle and second ends, transverse to the longitudinal axis and having a proximal and a distal edge with respect to the needle end of the flexible elongate base structure, a portion of said node's proximal edge relative said needle end of the flexible elongate base structure being perpendicular to the elongate base structure's longitudinal axis.

2. The process of claim 1 wherein said vessel is a fallopian tube.

3. The process of claim 2 wherein said fallopian tube is cinched sufficiently to block passage of an ovum through the fallopian tube's lumen, but is insufficiently occluded to unduly restrict blood circulation through said fallopian tube.

4. The process of claim 2 wherein said ligature is impregnated with contraceptive compound.

5. The process of claim 4 wherein said contraceptive compound is selected from the group of progestogens, estrogens, and mixtures thereof.

6. The process of claim 1 wherein said vessel is selected from the group of vessels consisting of vas deferens, veins, cystic ducts of a gall bladder, and arteries.

7. The process of claim 1 wherein the ligature further comprises a plurality of said nodes.

8. The process of claim 7 wherein said plurality of nodes is positioned in spaced relationship along the longitudinal axis of said base structure, and between a proximal edge of a first node and a distal edge of a second node, a planar notch exists.

9. The process of claim 1 wherein said elongate base structure is at least partially formed of a biodegradable material.

10. The process of claim 1 further including a needle associated with the needle end of the ligature.

11. The process of claim 1 wherein the ligature has a hinged flap positioned within said collar for allowing unidirectional movement of the base structure and associated node therethrough.

12. A process for occluding a fallopian tube comprising:

providing a ligature comprising:
    a flexible elongate base structure having a longitudinal axis, a needle end, and a second end,
    a collar for receiving a needle and affixed elongate base structure, positioned on said second end, and
    a node for interacting with the collar, said node positioned on said elongate base structure, between said needle and second end, transverse to the longitudinal axis and having a proximal and a distal edge with respect to the needle end of the flexible elongate base structure;

inserting said needle end through a mesosalpinx associated with said fallopian tube; encircling said fallopian tube with said ligature;

placing said needle end and affixed elongate base into the collar; and cinching said ligature about said fallopian tube to prevent passage of ova therethrough.

13. The process of claim 12 further comprising cinching a second ligature, in a spaced relationship along the fallopian tube from the first ligature, about said fallopian tube.

14. The process of claim 12 further comprising cutting through said fallopian tube.

15. The process of claim 12 wherein said process is conducted laparoscopically.

16. The process of claim 12 wherein said ligature further comprises an arced portion along the elongate base, such that when said ligature is cinched about said fallopian tube, a loop, non-contiguous with the fallopian tube, exists in said ligature.

17. The process of claim 12 wherein said ligature is formed of a biodegradable material, and said process is performed post-partum.

18. The process of claim 12 further comprising removing the needle end from the ligature.

19. An improvement in a tubal ligation of a vessel, said improvement comprising:

a temporary tubal ligation procedure comprising:
    using as ligature to perform the tubal ligation, a ligature made of a biodegradable material, said ligature comprising:
    a flexible elongate base structure having a longitudinal axis, a needle end, and
    a second end,
    a collar for receiving a needle and affixed elongate base structure, positioned on said second end, and
    a node for interacting with the collar, said node positioned on said elongate base structure, between said needle and second ends, transverse to the longitudinal axis and having a proximal and a distal edge with respect to the needle end of the flexible elongate base structure, a portion of said node's proximal edge relative said needle end of the flexible elongate base structure being perpendicular to the elongate base structure's longitudinal axis; and allowing said ligature to biodegrade, thus allowing the vessel to reopen.

20. The improvement of claim 19 wherein said biodegradable material is polylactic and glycolic acid.

* * * * *

UNITED STATES PATENT AND TRADEMARK OFFICE
CERTIFICATE OF CORRECTION

PATENT NO : 5,632,753
DATED : May 27, 1997
INVENTOR(S) : Loeser

It is certified that error appears in the above-identified patent and that said Letters Patent is hereby corrected as shown below:

In column 1, line 65, change "tureen" to --lumen--;
In column 2, lines 53-54, delete "according";
In column 3, line 28, change "curing" to --cutting--;
In column 6, line 46, insert a hyphen between "rubber" and "type".

Signed and Sealed this

Fourth Day of January, 2000

Attest:

Attesting Officer

*Acting Commissioner of Patents and Trademarks*